United States Patent [19]
Hillman et al.

[11] Patent Number: 5,858,719
[45] Date of Patent: Jan. 12, 1999

[54] POLYNUCLEOTIDES ENCODING HUMAN ATP BINDING-CASSETTE TRANSPORT PROTEIN AND METHODS OF USE

[75] Inventors: Jennifer L. Hillman, Mountain View; Purvi Shah, Sunnyvale; Neil C. Corley, Mountain View, all of Calif.

[73] Assignee: Incyte Pharmaceuticals, Inc., Palo Alto, Calif.

[21] Appl. No.: 895,522

[22] Filed: Jul. 17, 1997

[51] Int. Cl.⁶ .............................. C12P 21/06; C12Q 1/68; C12N 15/00; C07H 17/00
[52] U.S. Cl. ..................... 435/69.1; 435/6; 435/320.1; 435/252.3; 435/325; 536/23.1
[58] Field of Search ........................ 435/69.1, 6, 320.1, 435/252.3, 325; 536/23.1

[56] References Cited

PUBLICATIONS

Higgins, C.F., "ABC Transporters: From Microorganisms to Man", *Annu. Rev. Cell Biol.*, 8: 67–113 (1992).

Gottesman, M.M. et al., "Biochemistry of Multidrug Resistance Mediated by the Multidrug Transporter", *Annu. Rev. Biochem.*, 62: 385–427 (1993).

Ruetz, S. et al., "Phosphatidylcholine Translocase: A Physiological Role for the mdr2 Gene", *Cell*, 77: 1071–1081 (1994).

Welsh, M.J. et al., "Molecular Mechanisms of CFTR Chloride Channel Dysfunction in Cystic Fibrosis", *Cell*, 73:1251–1254 (1993).

Androlewicz, M.J. et al., "Characteristics of peptide and major histocompatibility complex class I/β–microglobulin binding to the transporters associated with antigen processing (TAP1 and TAP2)", *Proc. Natl. Acad. Sci. USA*, 91:12716–12720 (1994).

Büchler, M. et al., "cDNA Cloning of the Hepatocyte Canalicular Isoform of the Multidrug Resistance Protein, cMrp, Reveals a Novel Conjugate Export Pump Deficient in Hyperbilirubinemic Mutant Rats", *J. Biol. Chem.*, 271:15091–15098 (1996).

Michaelis, S., "STE6, the yeast a–factor transporter", *Semin. Cell Biol.*, 4: 17–27 (1993).

Savary, S. et al., "Isolation and Chromosomal mapping of a Novel ATP–Binding Cassette Transporter Conserved in Mouse and Human", *Genomics*, 41: 275–278 (1997) (GI 1167982).

Savary, S. et al., (Direct Submission), GenBank Sequence Database (Accession 1167982), National Center for Biotechnology Information, National Library of Medicine, Bethesda, Maryland, 20894 (GI 1167982).

Savary, S. et al., (Direct Submission), GenBank Sequence Database (Accession U43892), National Center for Biotechnology Information, National Library of Medicine, Bethesda, Maryland, 20894 (GI 1167982).

Leighton, J. et al., (Direct Submission), GenBank Sequence Database (Accession 575393), National Center for Biotechnology Information, National Library of Medicine, Bethesda, Maryland, 20894 (GI 575393).

Leighton, J. et al., (Direct Submission), GenBank Sequence Database (Accession X82612), National Center for Biotechnology Information, National Library of Medicine, Bethesda, Maryland, 20894 (GI 575393).

Leighton, J. et al., "An ABC transporter in the mitrochondrial inner membrane is required for normal growth of yeast", *EMBO J.*, 14: 188–195 (1995) (GI 575393).

*Primary Examiner*—Karen Cochrane Carlson
*Attorney, Agent, or Firm*—Incyte Pharmaceuticals, Inc; Lucy J. Billings; Sheela Mohan-Peterson

[57] ABSTRACT

The invention provides a human ATP-binding cassette transport protein (ABCtxH) and polynucleotides which identify and encode ABCtxH. The invention also provides expression vectors, host cells, agonists, antibodies and antagonists. The invention also provides methods for treating disorders associated with expression of ABCtxH.

10 Claims, 13 Drawing Sheets

```
                                                                                54
5'  TG CTC GCG ATG CAT TCT TGG CGC TGG GCT GCC GCG GCT TTC GAA AAG
       L   A   M   H   S   W   R   W   A   A   A   A   F   E   K

108
    CGC CGG CAC TCC GCG ATT CTG ATC CGG CCT TTA GCC GCG GCT TCT GTT AGC GGC TCA GGT
     R   R   H   S   A   I   L   I   R   P   L   A   A   A   S   V   S   G   S   G

162
    CCG CAG TGG AGG CCA CAT CAA CTC GGC GCC TTG ACC GCT CGA GCC TAC CAG
     P   Q   W   R   P   H   Q   L   G   A   L   T   A   R   A   Y   Q

216
    ATT CCA GAG TCA TTA AAA AGT ATC ACA TGG CAG AGA TTG GGA AAA GGC AAT TCA
     I   P   E   S   L   K   S   I   T   W   Q   R   L   G   K   G   N   S

270
    GGA CAG TTC TTA GAT GCT GCA AAG GCT CTC CAG GTA TGG CCA CTG ATA GAA AAG
     G   Q   F   L   D   A   A   K   A   L   Q   V   W   P   L   I   E   K

324
    AGG ACA TGT TGG CAT GGT CAT GCA GGA GGA CTC CAC ACA GAC CCA AAA GAA
     R   T   C   W   H   G   H   A   G   G   L   H   T   D   P   K   E

378
    GGG TTA AAA GAT GTT GAT ACT CGG AAA ATC ATA AAA GCA AAG CTT TCT TAT GTG
     G   L   K   D   V   D   T   R   K   I   I   K   A   K   L   S   Y   V

FIG. 1A
```

```
        387             396             405             414             423             432
TGG CCC AAA GAC AGG CCA GAT CTA CGA GCT AGA GTT GCC ATT TCG CTG GGA TTT
 W   P   K   D   R   P   D   L   R   A   R   V   A   I   S   L   G   F 441             450             459             468             477             486
TTG GGT GCA AAG GCC ATG AAT ATT GTG GTT CCC TTC ATG TTT AAA TAT GCT
 L   G   A   K   A   M   N   I   V   V   P   F   M   F   K   Y   A 495             504             513             522             531             540
GTA GAC AGC CTC AAC CAG ATG TCG GGA AAC ATG CTG AAC CTG AGT GAT GCA CCA
 V   D   S   L   N   Q   M   S   G   N   M   L   N   L   S   D   A   P 549             558             567             576             585             594
AAT ACA GTT GCA ACC ATG GCA ACA GCA GTT CTG ATT GGC TAT GGT GTA TCA AGA
 N   T   V   A   T   M   A   T   A   V   L   I   G   Y   G   V   S   R 603             612             621             630             639             648
GCT GGA GCT TTT AAC GAA GTT CGA AAT GCA GTA TTT GGC AAG GTA GCC
 A   G   A   F   N   E   V   R   N   A   V   F   G   K   V   A 657             666             675             684             693             702
CAG AAT TCA ATC CGA AGA ATA GCC AAA AAT GTC TTT CTC CAT CTT CAC AAC CTG
 Q   N   S   I   R   R   I   A   K   N   V   F   L   H   L   H   N   L 711             720             729             738             747             756
GAT CTG GGT TTT CAC CTG AGC AGA CAG ACG GGA GCT TTA TCT AAG GCT ATT GAC
 D   L   G   F   H   L   S   R   Q   T   G   A   L   S   K   A   I   D
```

FIG. 1B

```
      765           774           783           792           801           810
AGA GGA ACA AGG GGT ATC AGT TTT GTC CTG AGT TTT GCT TTG GTA TTT AAT CTT CTT
 R   G   T   R   G   I   S   F   V   L   S   F   A   L   V   F   N   L   L 819           828           837           846           855           864
CCC ATC ATG TTT GAA GTG ATG CTT GTC AGT GGT GTT TTG TAT TAC AAA TGC GGT
 P   I   M   F   E   V   M   L   V   S   G   V   L   Y   Y   K   C   G 873           882           891           900           909           918
GCC CAG TTT GCT TTG GTA ACC CTT GGA ACA CTT GGT ACA TAC ACA GCA TTC ACA
 A   Q   F   A   L   V   T   L   G   T   L   G   T   Y   T   A   F   T 927           936           945           954           963           972
GTT GCA GTC ACA CGG TGG AGA ACT AGA TTT AGA ATA GAA ATG AAC AAA GCA GAT
 V   A   V   T   R   W   R   T   R   F   R   I   E   M   N   K   A   D 981           990           999           1008          1017          1026
AAT GAT GCA GGT AAT GCT GCT ATA GAC TCA CTG CTG AAT TAT GAA ACT GTG AAG
 N   D   A   G   N   A   A   I   D   S   L   L   N   Y   E   T   V   K 1035          1044          1053          1062          1071          1080
TAT TTT AAT AAT GAA AGA TAT GAA GCA CAG AGA TAT GAT GGA TTT TTG AAG ACG
 Y   F   N   N   E   R   Y   E   A   Q   R   Y   D   G   F   L   K   T 1089          1098          1107          1116          1125          1134
TAT GAG ACT GCT TCA TTG AAA AGT ACC TCT ACT CTG GCT ATG CTG AAC TTT GGT
 Y   E   T   A   S   L   K   S   T   S   T   L   A   M   L   N   F   G
```

FIG. 1C

```
      1143            1152            1161            1170            1179            1188
CAA AGT GCT ATT TTC AGT GTC GGT TTA ACA GCT ATA ATG GTG CTC GCC AGT CAG
 Q   S   A   I   F   S   V   G   L   T   A   I   M   V   L   A   S   Q 1197            1206            1215            1224            1233            1242
GGA ATT GTG GCA GGT ACC CTT ACT GTT GGA GAT CTA GTA ATG GTG AAT GGA CTG
 G   I   V   A   G   T   L   T   V   G   D   L   V   M   V   N   G   L 1251            1260            1269            1278            1287            1296
CTT TTT CAG CTT TCA CCC CTG AAC TTT CTG GGA ACT GTA TAT AGA GAG ACT
 L   F   Q   L   S   P   L   N   F   L   G   T   V   Y   R   E   T 1305            1314            1323            1332            1341            1350
AGA CAA GCA CTC ATA GAT ATG AAC ACC TTG TTT ACT CTA CTC AAG GTA GAC ACC
 R   Q   A   L   I   D   M   N   T   L   F   T   L   L   K   V   D   T 1359            1368            1377            1386            1395            1404
CAA ATT AAA GAC AAA GTG ATG GCA TCT CCC CTT CAG ATC ACA CCA CAG ACA GCT
 Q   I   K   D   K   V   M   A   S   P   L   Q   I   T   P   Q   T   A 1413            1422            1431            1440            1449            1458
ACC GTG GCC TTT GAT AAT GTG CAT TTT GAA TAC ATT GAG GGC CAG AAA GTC CTT
 T   V   A   F   D   N   V   H   F   E   Y   I   E   G   Q   K   V   L 1467            1476            1485            1494            1503            1512
AGT GGA ATA TCC TTT GAA GTC CCT GCA GGA AAG GTG GCC ATT GTA GGA GGT
 S   G   I   S   F   E   V   P   A   G   K   V   A   I   V   G   G

FIG. 1D
```

```
1521            1530            1539            1548            1557            1566
AGT GGG TCA GGG AAA AGC ACA ATA GTG AGG CTA TTA TTT CGC TTC TAT GAG CCT
 S   G   S   G   K   S   T   I   V   R   L   L   F   R   F   Y   E   P 1575            1584            1593            1602            1611            1620
CAA AAG GGT AGC ATT TAT CTT GCT GGT CAA AAT ATA CAA GAT GTG AGC CTG GAA
 Q   K   G   S   I   Y   L   A   G   Q   N   I   Q   D   V   S   L   E 1629            1638            1647            1656            1665            1674
AGC CTT CGG AGG GCA GTG GGA GTG GTA CCT CAG GAT GCT GTC CTC TTC CAT AAT
 S   L   R   R   A   V   G   V   V   P   Q   D   A   V   L   F   H   N 1683            1692            1701            1710            1719            1728
ACT ATT TAT TAC AAC CTC TTA TAT GGA AAC ATC AGT GCT TCA CCC GAG GAA GTG
 T   I   Y   Y   N   L   L   Y   G   N   I   S   A   S   P   E   E   V 1737            1746            1755            1764            1773            1782
TAT GCA GTG GCA AAA TTA GCT GGA CTT CAT GAT GCA ATT CTT CGA ATG CCA CAT
 Y   A   V   A   K   L   A   G   L   H   D   A   I   L   R   M   P   H 1791            1800            1809            1818            1827            1836
GGA TAT GAC ACC CAA GTA GGG GAA CGA GGA CTC AAG CTT TCA GGA GGA GAA AAG
 G   Y   D   T   Q   V   G   E   R   G   L   K   L   S   G   G   E   K 1845            1854            1863            1872            1881            1890
CAA AGA GTA GCA ATT GCA AGA GCC ATT TTG AAG GAC CCC CCA GTC ATA CTC TAT
 Q   R   V   A   I   A   R   A   I   L   K   D   P   P   V   I   L   Y
```

FIG. 1E

```
              1899           1908           1917           1926           1935           1944
GAT GAA GCT ACT TCA TCG TTA GAT TCG ATT ACT GAA GAG ACT ATT CTT GGT GCC
 D   E   A   T   S   S   L   D   S   I   T   E   E   T   I   L   G   A 1953           1962           1971           1980           1989           1998
ATG AAG GAT GTG GTC AAA CAC AGA ACT TCT ATT TTC ATT GCA CAC AGA TTG TCA
 M   K   D   V   V   K   H   R   T   S   I   F   I   A   H   R   L   S 2007           2016           2025           2034           2043           2052
ACA GTG GTT GAT GCA GAT GAA ATC ATT GTC TTG GAT CAG GGT AAG GTA GCC GAA
 T   V   V   D   A   D   E   I   I   V   L   D   Q   G   K   V   A   E 2061           2070           2079           2088           2097           2106
CGT GGT ACC CAC CAT GGT TTG CTT GCT AAC CCT CAT AGT ATC TAT TCA GAA ATG
 R   G   T   H   H   G   L   L   A   N   P   H   S   I   Y   S   E   M 2115           2124           2133           2142           2151           2160
TGG CAT ACA CAG AGC AGC CGT GTG CAG AAC CAT GAT AAC CCC AAA TGG GAA GCA
 W   H   T   Q   S   S   R   V   Q   N   H   D   N   P   K   W   E   A 2169           2178           2187           2196           2205           2214
AAG AAA GAA AAT ATA TCC AAA GAG GAG GAA AGA AAG AAA CTA CAA GAA GAA ATT
 K   K   E   N   I   S   K   E   E   E   R   K   K   L   Q   E   E   I 2223           2232           2241           2250           2259           2268
GTC AAT AGT GTG AAA GGC TGT GGA AAC TGT TCG TGC TAG TCA CAT AGA CAT NTC
 V   N   S   V   K   G   C   G   N   C   S   C   *   S   H   R   H   X
```

FIG. 1F

```
     2277           2286           2295           2304           2313           2322
TNT NTT GTT GTN TGG ACT AAT ATT GCA CTG AAC AAA TGT TTA TTA AAA ATC AAA
     2331           2340           2349           2358           2367           2376
TCC CAA AAA AAA AAA AAA AGG GCG CCC TTA AAG ACC CAG AGG CNA ACT TCC
     2385           2394           2403
CTG TAG CAA TTA ACC TCC CAT GAT ATA AAA AA 3'
```

FIG. 1G

| | | |
|---|---|---|
| 1 | M H S W R W A A A A A A F E K R R H S A | 545981 |
| 1 | - - - - - - - - - - - - - - - - - - - - | GI 1167982 |
| 1 | M L L L P R C P V I G R I V R S K F R S | GI 575393 |
| | | |
| 21 | I L I R P L V S V S G S G P Q W R P H Q | 545981 |
| 1 | - - - - - - - - - - - - - - - - - - - - | GI 1167982 |
| 21 | G L I R N H S R N H S P V I - - - - F T | GI 575393 |
| | | |
| 41 | L G A L G T A R A - - Y Q I P E S L K S | 545981 |
| 1 | - - - - - - - - - - - - - - - E S L R N | GI 1167982 |
| 37 | V S K L S T Q R P L L F N S A V N L W N | GI 575393 |
| | | |
| 59 | I T W Q R L G K G N S G Q F L D A A K A | 545981 |
| 6 | T T Q Q R W G K D N S R Q L L D A T K A | GI 1167982 |
| 57 | Q A Q K D I T H K K S V E Q F S S A P K | GI 575393 |
| | | |
| 79 | L Q V W P L I E K R T C W H G H A G G G | 545981 |
| 26 | L Q T W P L I E K R T C W H G H A G G G | GI 1167982 |
| 77 | V K T - - Q V K K - - - - - - - - - - - | GI 575393 |
| | | |
| 99 | L H T D P K E G L K D V D T R K I I K A | 545981 |
| 46 | L H T D P K E G L K D V D T R K I I K A | GI 1167982 |
| 84 | - - T S K A P T L S E L - - - K I L K D | GI 575393 |
| | | |
| 119 | K L S Y V W P K D R P D L R A R V A I S | 545981 |
| 66 | M L S Y V W P E D R P D L R A R V A I S | GI 1167982 |
| 99 | L F R Y I W P K G N N K V R I R V L I A | GI 575393 |
| | | |
| 139 | L G F L G G A K A M N I V V P F M F K Y | 545981 |
| 86 | L G F L G G A K A M N I V V P F M F K Y | GI 1167982 |
| 119 | L G L L I S A K I L N V Q V P F F F K Q | GI 575393 |
| | | |
| 159 | A V D S L N Q M S G N M L N L S D A P N | 545981 |
| 106 | A V D S L N Q M S G N M L N L S D A P N | GI 1167982 |
| 139 | T I D S M N - - - - - - - I A W D D P T V | GI 575393 |

FIG. 2A

| | | |
|---|---|---|
| 179 | T V A T M A T A V L I G Y G V S R A G A | 545981 |
| 126 | T V A T M A T A V L I G Y G V S R A G A | GI 1167982 |
| 153 | A L P A A I G L T I L C Y G V A R F G S | GI 575393 |

| | | |
|---|---|---|
| 199 | A F F N E V R N A V F G K V A Q N S I R | 545981 |
| 146 | A F F N E V R N A V F G K V A Q N S I R | GI 1167982 |
| 173 | V L F G E L R N A V F A K V A Q N A I R | GI 575393 |

| | | |
|---|---|---|
| 219 | R I A K N V F L H L H N L D L G F H L S | 545981 |
| 166 | R I A K N V F L H L H N L D L G F H L S | GI 1167982 |
| 193 | T V S L Q T F Q H L M K L D L G W H L S | GI 575393 |

| | | |
|---|---|---|
| 239 | R Q T G A L S K A I D R G T R G I S F V | 545981 |
| 186 | R Q T G A L S K A I D R G T R G I S F V | GI 1167982 |
| 213 | R Q T G G L T R A M D R G T K G I S Q V | GI 575393 |

| | | |
|---|---|---|
| 259 | L S A L V F N L L P I M F E V M L V S G | 545981 |
| 206 | L S A L V F N L L P I V F E M M L V S S | GI 1167982 |
| 233 | L T A M V F H I I P I S F E I S V V C G | GI 575393 |

| | | |
|---|---|---|
| 279 | V L Y Y K C G A Q F A L V T L G T L G T | 545981 |
| 226 | V L Y Y K C G A Q F A L V T L G T L G A | GI 1167982 |
| 253 | I L T Y Q F G A S F A A I T F S T M L L | GI 575393 |

| | | |
|---|---|---|
| 299 | Y T A F T V A V T R W R T R F R I E M N | 545981 |
| 246 | Y T A F T V A V T R W R T R F R I E M N | GI 1167982 |
| 273 | Y S I F T I K T T A W R T H F R R D A N | GI 575393 |

| | | |
|---|---|---|
| 319 | K A D N D A G N A A I D S L L N Y E T V | 545981 |
| 266 | K A D N D A G N A A I D S L L N Y E T V | GI 1167982 |
| 293 | K A D N K A A S V A L D S L I N F E A V | GI 575393 |

| | | |
|---|---|---|
| 339 | K Y F N N E R Y E A Q R Y D G F L K T Y | 545981 |
| 286 | K Y F N N E K Y E A Q R Y D G F L K T Y | GI 1167982 |
| 313 | K Y F N N E K Y L A D K Y N G S L M N Y | GI 575393 |

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 747 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: OVARNOT02
        ( B ) CLONE: 545981

( x i ) SEQUENCE DESCRIPTION: SEQ ID NO:1:

```
Met His Ser Trp Arg Trp Ala Ala Ala Ala Ala Phe Glu Lys Arg
  1           5                  10                  15

Arg His Ser Ala Ile Leu Ile Arg Pro Leu Val Ser Val Ser Gly Ser
              20                  25                  30

Gly Pro Gln Trp Arg Pro His Gln Leu Gly Ala Leu Gly Thr Ala Arg
              35                  40                  45

Ala Tyr Gln Ile Pro Glu Ser Leu Lys Ser Ile Thr Trp Gln Arg Leu
      50                  55                  60

Gly Lys Gly Asn Ser Gly Gln Phe Leu Asp Ala Ala Lys Ala Leu Gln
 65                  70                  75                  80

Val Trp Pro Leu Ile Glu Lys Arg Thr Cys Trp His Gly His Ala Gly
                  85                  90                  95

Gly Gly Leu His Thr Asp Pro Lys Glu Gly Leu Lys Asp Val Asp Thr
                 100                 105                 110

Arg Lys Ile Ile Lys Ala Lys Leu Ser Tyr Val Trp Pro Lys Asp Arg
             115                 120                 125

Pro Asp Leu Arg Ala Arg Val Ala Ile Ser Leu Gly Phe Leu Gly Gly
         130                 135                 140

Ala Lys Ala Met Asn Ile Val Val Pro Phe Met Phe Lys Tyr Ala Val
145                 150                 155                 160

Asp Ser Leu Asn Gln Met Ser Gly Asn Met Leu Asn Leu Ser Asp Ala
                 165                 170                 175

Pro Asn Thr Val Ala Thr Met Ala Thr Ala Val Leu Ile Gly Tyr Gly
             180                 185                 190

Val Ser Arg Ala Gly Ala Ala Phe Phe Asn Glu Val Arg Asn Ala Val
         195                 200                 205

Phe Gly Lys Val Ala Gln Asn Ser Ile Arg Arg Ile Ala Lys Asn Val
210                 215                 220

Phe Leu His Leu His Asn Leu Asp Leu Gly Phe His Leu Ser Arg Gln
225                 230                 235                 240

Thr Gly Ala Leu Ser Lys Ala Ile Asp Arg Gly Thr Arg Gly Ile Ser
                 245                 250                 255

Phe Val Leu Ser Ala Leu Val Phe Asn Leu Leu Pro Ile Met Phe Glu
             260                 265                 270

Val Met Leu Val Ser Gly Val Leu Tyr Tyr Lys Cys Gly Ala Gln Phe
         275                 280                 285

Ala Leu Val Thr Leu Gly Thr Leu Gly Thr Tyr Thr Ala Phe Thr Val
         290                 295                 300

Ala Val Thr Arg Trp Arg Thr Arg Phe Arg Ile Glu Met Asn Lys Ala
```

|  | 305 |  |  |  | 310 |  |  |  | 315 |  |  |  | 320 |  |  |  |
| --- | --- | --- | --- | --- | --- | --- | --- | --- | --- | --- | --- | --- | --- | --- | --- | --- |

Asp Asn Asp Ala Gly Asn Ala Ala Ile Asp Ser Leu Leu Asn Tyr Glu
                    325                     330                    335

Thr Val Lys Tyr Phe Asn Asn Glu Arg Tyr Glu Ala Gln Arg Tyr Asp
                340                     345                     350

Gly Phe Leu Lys Thr Tyr Glu Thr Ala Ser Leu Lys Ser Thr Ser Thr
            355                     360                 365

Leu Ala Met Leu Asn Phe Gly Gln Ser Ala Ile Phe Ser Val Gly Leu
        370                     375                 380

Thr Ala Ile Met Val Leu Ala Ser Gln Gly Ile Val Ala Gly Thr Leu
385                     390                     395                     400

Thr Val Gly Asp Leu Val Met Val Asn Gly Leu Leu Phe Gln Leu Ser
                405                     410                     415

Leu Pro Leu Asn Phe Leu Gly Thr Val Tyr Arg Glu Thr Arg Gln Ala
                420                     425                 430

Leu Ile Asp Met Asn Thr Leu Phe Thr Leu Leu Lys Val Asp Thr Gln
            435                     440                 445

Ile Lys Asp Lys Val Met Ala Ser Pro Leu Gln Ile Thr Pro Gln Thr
        450                     455                 460

Ala Thr Val Ala Phe Asp Asn Val His Phe Glu Tyr Ile Glu Gly Gln
465                     470                     475                     480

Lys Val Leu Ser Gly Ile Ser Phe Glu Val Pro Ala Gly Lys Lys Val
                485                     490                     495

Ala Ile Val Gly Gly Ser Gly Ser Gly Lys Ser Thr Ile Val Arg Leu
            500                     505                 510

Leu Phe Arg Phe Tyr Glu Pro Gln Lys Gly Ser Ile Tyr Leu Ala Gly
        515                     520                 525

Gln Asn Ile Gln Asp Val Ser Leu Glu Ser Leu Arg Arg Ala Val Gly
    530                     535                 540

Val Val Pro Gln Asp Ala Val Leu Phe His Asn Thr Ile Tyr Tyr Asn
545                     550                     555                     560

Leu Leu Tyr Gly Asn Ile Ser Ala Ser Pro Glu Glu Val Tyr Ala Val
                565                     570                     575

Ala Lys Leu Ala Gly Leu His Asp Ala Ile Leu Arg Met Pro His Gly
            580                     585                 590

Tyr Asp Thr Gln Val Gly Glu Arg Gly Leu Lys Leu Ser Gly Gly Glu
        595                     600                 605

Lys Gln Arg Val Ala Ile Ala Arg Ala Ile Leu Lys Asp Pro Pro Val
    610                     615                 620

Ile Leu Tyr Asp Glu Ala Thr Ser Ser Leu Asp Ser Ile Thr Glu Glu
625                     630                     635                     640

Thr Ile Leu Gly Ala Met Lys Asp Val Val Lys His Arg Thr Ser Ile
                645                     650                     655

Phe Ile Ala His Arg Leu Ser Thr Val Val Asp Ala Asp Glu Ile Ile
            660                     665                 670

Val Leu Asp Gln Gly Lys Val Ala Glu Arg Gly Thr His His Gly Leu
        675                     680                 685

Leu Ala Asn Pro His Ser Ile Tyr Ser Glu Met Trp His Thr Gln Ser
    690                     695                 700

Ser Arg Val Gln Asn His Asp Asn Pro Lys Trp Glu Ala Lys Lys Glu
705                     710                     715                     720

Asn Ile Ser Lys Glu Glu Arg Lys Lys Leu Gln Glu Glu Ile Val
                725                     730                     735

| Asn | Ser | Val | Lys | Gly | Cys | Gly | Asn | Cys | Ser | Cys |
|-----|-----|-----|-----|-----|-----|-----|-----|-----|-----|-----|
|     |     |     | 740 |     |     |     |     | 745 |     |     |

(2) INFORMATION FOR SEQ ID NO:2:

(i) SEQUENCE CHARACTERISTICS:
        (A) LENGTH: 2407 base pairs
        (B) TYPE: nucleic acid
        (C) STRANDEDNESS: single
        (D) TOPOLOGY: linear (vii) IMMEDIATE SOURCE:
        (A) LIBRARY: OVARNOT02
        (B) CLONE: 545981

(xi) SEQUENCE DESCRIPTION: SEQ ID NO:2:

```
TGCTCGCGAT GCATTCTTGG CGCTGGGCTG CCGCGGCGGC TGCTTTCGAA AAGCGCCGGC      60
ACTCCGCGAT TCTGATCCGG CCTTTAGTCT CTGTTAGCGG CTCAGGTCCG CAGTGGAGGC     120
CACATCAACT CGGCGCCTTG GGAACCGCTC GAGCCTACCA GATTCCAGAG TCATTAAAAA     180
GTATCACATG GCAGAGATTG GGAAAAGGCA ATTCAGGACA GTTCTTAGAT GCTGCAAAGG     240
CTCTCCAGGT ATGGCCACTG ATAGAAAAGA GGACATGTTG GCATGGTCAT GCAGGAGGAG     300
GACTCCACAC AGACCCAAAA GAAGGGTTAA AAGATGTTGA TACTCGGAAA ATCATAAAAG     360
CAAAGCTTTC TTATGTGTGG CCCAAAGACA GGCCAGATCT ACGAGCTAGA GTTGCCATTT     420
CGCTGGGATT TTTGGGTGGT GCAAAGGCCA TGAATATTGT GGTTCCCTTC ATGTTTAAAT     480
ATGCTGTAGA CAGCCTCAAC CAGATGTCGG GAAACATGCT GAACCTGAGT GATGCACCAA     540
ATACAGTTGC AACCATGGCA ACAGCAGTTC TGATTGGCTA TGGTGTATCA AGAGCTGGAG     600
CTGCTTTTTT TAACGAAGTT CGAAATGCAG TATTTGGCAA GGTAGCCCAG AATTCAATCC     660
GAAGAATAGC CAAAAATGTC TTTCTCCATC TTCACAACCT GGATCTGGGT TTTCACCTGA     720
GCAGACAGAC GGGAGCTTTA TCTAAGGCTA TTGACAGAGG AACAAGGGGT ATCAGTTTTG     780
TCCTGAGTGC TTTGGTATTT AATCTTCTTC CCATCATGTT TGAAGTGATG CTTGTCAGTG     840
GTGTTTTGTA TTACAAATGC GGTGCCCAGT TTGCTTTGGT AACCCTTGGA ACACTTGGTA     900
CATACACAGC ATTCACAGTT GCAGTCACAC GGTGGAGAAC TAGATTTAGA ATAGAAATGA     960
ACAAAGCAGA TAATGATGCA GGTAATGCTG CTATAGACTC ACTGCTGAAT TATGAAACTG    1020
TGAAGTATTT TAATAATGAA AGATATGAAG CACAGAGATA TGATGGATTT TTGAAGACGT    1080
ATGAGACTGC TTCATTGAAA AGTACCTCTA CTCTGGCTAT GCTGAACTTT GGTCAAAGTG    1140
CTATTTTCAG TGTCGGTTTA ACAGCTATAA TGGTGCTCGC CAGTCAGGGA ATTGTGGCAG    1200
GTACCCTTAC TGTTGGAGAT CTAGTAATGG TGAATGGACT GCTTTTTCAG CTTTCATTAC    1260
CCCTGAACTT TCTGGGAACT GTATATAGAG AGACTAGACA AGCACTCATA GATATGAACA    1320
CCTTGTTTAC TCTACTCAAG GTAGACACCC AAATTAAAGA CAAAGTGATG GCATCTCCCC    1380
TTCAGATCAC ACCACAGACA GCTACCGTGG CCTTTGATAA TGTGCATTTT GAATACATTG    1440
AGGGCCAGAA AGTCCTTAGT GGAATATCCT TTGAAGTCCC TGCAGGAAAG AAAGTGGCCA    1500
TTGTAGGAGG TAGTGGGTCA GGGAAAAGCA CAATAGTGAG GCTATTATTT CGCTTCTATG    1560
AGCCTCAAAA GGGTAGCATT TATCTTGCTG GTCAAAATAT ACAAGATGTG AGCCTGGAAA    1620
GCCTTCGGAG GGCAGTGGGA GTGGTACCTC AGGATGCTGT CCTCTTCCAT AATACTATTT    1680
ATTACAACCT CTTATATGGA AACATCAGTG CTTCACCCGA GGAAGTGTAT GCAGTGGCAA    1740
AATTAGCTGG ACTTCATGAT GCAATTCTTC GAATGCCACA TGGATATGAC ACCCAAGTAG    1800
GGGAACGAGG ACTCAAGCTT TCAGGAGGAG AAAAGCAAAG AGTAGCAATT GCAAGAGCCA    1860
```

-continued

```
TTTTGAAGGA CCCCCCAGTC ATACTCTATG ATGAAGCTAC TTCATCGTTA GATTCGATTA      1920
CTGAAGAGAC TATTCTTGGT GCCATGAAGG ATGTGGTCAA ACACAGAACT TCTATTTTCA      1980
TTGCACACAG ATTGTCAACA GTGGTTGATG CAGATGAAAT CATTGTCTTG GATCAGGGTA      2040
AGGTAGCCGA ACGTGGTACC CACCATGGTT TGCTTGCTAA CCCTCATAGT ATCTATTCAG      2100
AAATGTGGCA TACACAGAGC AGCCGTGTGC AGAACCATGA TAACCCCAAA TGGGAAGCAA      2160
AGAAAGAAAA TATATCCAAA GAGGAGGAAA GAAAGAAACT ACAAGAAGAA ATTGTCAATA      2220
GTGTGAAAGG CTGTGGAAAC TGTTCGTGCT AGTCACATAG ACATNTCTNT NTTGTTGTNT      2280
GGACTAATAT TGCACTGAAC AAATGTTTAT TAAAAATCAA ATCCCAAAAA AAAAAAAAA      2340
AAAGGGCGCC CTTAAAGACC CAGAGGCNAA CTTCCCTGTA GCAATTAACC TCCCATGATA      2400
TAAAAAA                                                                2407
```

( 2 ) INFORMATION FOR SEQ ID NO:3:

( i ) SEQUENCE CHARACTERISTICS:
        ( A ) LENGTH: 694 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1167982

( x i ) SEQUENCE DESCRIPTION: SEQ ID NO:3:

```
Glu Ser Leu Arg Asn Thr Thr Gln Gln Arg Trp Gly Lys Asp Asn Ser
 1               5                  10                  15
Arg Gln Leu Leu Asp Ala Thr Lys Ala Leu Gln Thr Trp Pro Leu Ile
            20                  25                  30
Glu Lys Arg Thr Cys Trp His Gly His Ala Gly Gly Gly Leu His Thr
        35                  40                  45
Asp Pro Lys Glu Gly Leu Lys Asp Val Asp Thr Arg Lys Ile Ile Lys
    50                  55                  60
Ala Met Leu Ser Tyr Val Trp Pro Glu Asp Arg Pro Asp Leu Arg Ala
65                  70                  75                  80
Arg Val Ala Ile Ser Leu Gly Phe Leu Gly Gly Ala Lys Ala Met Asn
                85                  90                  95
Ile Val Val Pro Phe Met Phe Lys Tyr Ala Val Asp Ser Leu Asn Gln
            100                 105                 110
Met Ser Gly Asn Met Leu Asn Leu Ser Asp Ala Pro Asn Thr Val Ala
        115                 120                 125
Thr Met Ala Thr Ala Val Leu Ile Gly Tyr Gly Val Ser Arg Ala Gly
    130                 135                 140
Ala Ala Phe Phe Asn Glu Val Arg Asn Ala Val Phe Gly Lys Val Ala
145                 150                 155                 160
Gln Asn Ser Ile Arg Arg Ile Ala Lys Asn Val Phe Leu His Leu His
                165                 170                 175
Asn Leu Asp Leu Gly Phe His Leu Ser Arg Gln Thr Gly Ala Leu Ser
            180                 185                 190
Lys Ala Ile Asp Arg Gly Thr Arg Gly Ile Ser Phe Val Leu Ser Ala
        195                 200                 205
Leu Val Phe Asn Leu Leu Pro Ile Val Phe Glu Met Met Leu Val Ser
    210                 215                 220
Ser Val Leu Tyr Tyr Lys Cys Gly Ala Gln Phe Ala Leu Val Thr Leu
225                 230                 235                 240
```

```
Gly  Thr  Leu  Gly  Ala  Tyr  Thr  Ala  Phe  Thr  Val  Ala  Val  Thr  Arg  Trp
               245                      250                     255

Arg  Thr  Arg  Phe  Arg  Ile  Glu  Met  Asn  Lys  Ala  Asp  Asn  Asp  Ala  Gly
               260                 265                     270

Asn  Ala  Ala  Ile  Asp  Ser  Leu  Leu  Asn  Tyr  Glu  Thr  Val  Lys  Tyr  Phe
               275                 280                     285

Asn  Asn  Glu  Lys  Tyr  Glu  Ala  Gln  Arg  Tyr  Asp  Gly  Phe  Leu  Lys  Thr
     290                      295                     300

Tyr  Glu  Thr  Ala  Ser  Leu  Lys  Ser  Thr  Ser  Thr  Leu  Ala  Met  Leu  Asn
305                           310                 315                     320

Phe  Gly  Gln  Asn  Ala  Ile  Phe  Ser  Val  Gly  Leu  Thr  Ala  Ile  Met  Val
                    325                 330                          335

Leu  Ala  Ser  Gln  Gly  Ile  Val  Ala  Gly  Ala  Leu  Thr  Val  Gly  Asp  Leu
               340                      345                     350

Val  Met  Val  Asn  Gly  Leu  Leu  Phe  Gln  Leu  Ser  Leu  Pro  Leu  Asn  Phe
               355                 360                     365

Leu  Gly  Thr  Val  Tyr  Arg  Glu  Thr  Arg  Gln  Ala  Leu  Ile  Asp  Met  Asn
     370                      375                     380

Thr  Leu  Phe  Thr  Leu  Leu  Lys  Val  Asp  Thr  Arg  Ile  Lys  Asp  Lys  Val
385                      390                     395                      400

Met  Ala  Pro  Pro  Leu  Gln  Ile  Thr  Pro  Gln  Thr  Ala  Thr  Val  Ala  Phe
                    405                      410                          415

Asp  Asn  Val  His  Phe  Glu  Tyr  Ile  Glu  Gly  Gln  Lys  Val  Leu  Asn  Gly
               420                 425                     430

Val  Ser  Phe  Glu  Val  Pro  Ala  Gly  Lys  Lys  Val  Ala  Ile  Val  Gly  Gly
          435                      440                     445

Ser  Gly  Ser  Gly  Lys  Ser  Thr  Ile  Val  Arg  Leu  Leu  Phe  Arg  Phe  Tyr
450                           455                     460

Glu  Pro  Gln  Lys  Gly  Ser  Ile  Tyr  Leu  Ala  Gly  Gln  Asn  Leu  Gln  Asp
465                      470                     475                      480

Val  Ser  Leu  Glu  Ser  Leu  Arg  Arg  Ala  Val  Gly  Val  Val  Pro  Gln  Asp
               485                      490                     495

Ala  Val  Leu  Phe  His  Asn  Thr  Ile  Tyr  Tyr  Asn  Leu  Leu  Tyr  Gly  Asn
               500                 505                     510

Ile  Asn  Ala  Ser  Pro  Glu  Glu  Val  Tyr  Ala  Val  Ala  Lys  Leu  Ala  Gly
          515                      520                     525

Leu  His  Asp  Ala  Ile  Leu  Arg  Met  Pro  His  Gly  Tyr  Asp  Thr  Gln  Val
     530                      535                     540

Gly  Glu  Arg  Gly  Leu  Lys  Leu  Ser  Gly  Gly  Glu  Lys  Gln  Arg  Val  Ala
545                      550                     555                      560

Ile  Ala  Arg  Ala  Ile  Leu  Lys  Asn  Pro  Pro  Val  Ile  Leu  Tyr  Asp  Glu
               565                      570                     575

Ala  Thr  Ser  Ser  Leu  Asp  Ser  Ile  Thr  Glu  Glu  Thr  Ile  Leu  Gly  Ala
               580                 585                     590

Met  Arg  Asp  Val  Val  Lys  His  Arg  Thr  Ser  Ile  Phe  Ile  Ala  His  Arg
     595                      600                     605

Leu  Ser  Thr  Val  Val  Asp  Ala  Asp  Glu  Ile  Ile  Val  Leu  Ser  Gln  Gly
     610                      615                     620

Lys  Val  Ala  Glu  Arg  Gly  Thr  His  Tyr  Gly  Leu  Leu  Ala  Asn  Ser  Ser
625                           630                     635                 640

Ser  Ile  Tyr  Ser  Glu  Met  Trp  His  Thr  Gln  Ser  Asn  Arg  Val  Gln  Asn
                    645                      650                     655

Gln  Asp  Ser  Leu  Gly  Trp  Asp  Ala  Lys  Lys  Glu  Ser  Leu  Ser  Lys  Glu
               660                      665                     670
```

```
Glu Glu Arg Lys Lys Leu Gln Glu Glu Ile Val Asn Ser Val Lys Gly
            675                 680                 685

Cys Gly Asn Cys Ser Cys
            690
```

( 2 ) INFORMATION FOR SEQ ID NO:4:

( i ) SEQUENCE CHARACTERISTICS:
        ( A ) LENGTH: 694 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 575393

( x i ) SEQUENCE DESCRIPTION: SEQ ID NO:4:

```
Met Leu Leu Leu Pro Arg Cys Pro Val Ile Gly Arg Ile Val Arg Ser
 1               5                  10                  15

Lys Phe Arg Ser Gly Leu Ile Arg Asn His Ser Arg Asn His Ser Pro
            20                  25                  30

Val Ile Phe Thr Val Ser Lys Leu Ser Thr Gln Arg Pro Leu Leu Phe
            35                  40                  45

Asn Ser Ala Val Asn Leu Trp Asn Gln Ala Gln Lys Asp Ile Thr His
     50                  55                  60

Lys Lys Ser Val Glu Gln Phe Ser Ser Ala Pro Lys Val Lys Thr Gln
65                   70                  75                  80

Val Lys Lys Thr Ser Lys Ala Pro Thr Leu Ser Glu Leu Lys Ile Leu
                 85                  90                  95

Lys Asp Leu Phe Arg Tyr Ile Trp Pro Lys Gly Asn Asn Lys Val Arg
                100                 105                 110

Ile Arg Val Leu Ile Ala Leu Gly Leu Leu Ile Ser Ala Lys Ile Leu
            115                 120                 125

Asn Val Gln Val Pro Phe Phe Phe Lys Gln Thr Ile Asp Ser Met Asn
     130                 135                 140

Ile Ala Trp Asp Asp Pro Thr Val Ala Leu Pro Ala Ala Ile Gly Leu
145                 150                 155                 160

Thr Ile Leu Cys Tyr Gly Val Ala Arg Phe Gly Ser Val Leu Phe Gly
                165                 170                 175

Glu Leu Arg Asn Ala Val Phe Ala Lys Val Ala Gln Asn Ala Ile Arg
            180                 185                 190

Thr Val Ser Leu Gln Thr Phe Gln His Leu Met Lys Leu Asp Leu Gly
            195                 200                 205

Trp His Leu Ser Arg Gln Thr Gly Gly Leu Thr Arg Ala Met Asp Arg
     210                 215                 220

Gly Thr Lys Gly Ile Ser Gln Val Leu Thr Ala Met Val Phe His Ile
225                 230                 235                 240

Ile Pro Ile Ser Phe Glu Ile Ser Val Val Cys Gly Ile Leu Thr Tyr
                245                 250                 255

Gln Phe Gly Ala Ser Phe Ala Ala Ile Thr Phe Ser Thr Met Leu Leu
            260                 265                 270

Tyr Ser Ile Phe Thr Ile Lys Thr Thr Ala Trp Arg Thr His Phe Arg
            275                 280                 285

Arg Asp Ala Asn Lys Ala Asp Asn Lys Ala Ala Ser Val Ala Leu Asp
     290                 295                 300

Ser Leu Ile Asn Phe Glu Ala Val Lys Tyr Phe Asn Asn Glu Lys Tyr
```

-continued

```
305                  310                  315                  320
Leu Ala Asp Lys Tyr Asn Gly Ser Leu Met Asn Tyr Arg Asp Ser Gln
                325                 330                 335
Ile Lys Val Ser Gln Ser Leu Ala Phe Leu Asn Ser Gly Gln Asn Leu
                340                 345                 350
Ile Phe Thr Thr Ala Leu Thr Ala Met Met Tyr Met Gly Cys Thr Gly
                355                 360                 365
Val Ile Gly Gly Asn Leu Thr Val Gly Asp Leu Val Leu Ile Asn Gln
        370                 375                 380
Leu Val Phe Gln Leu Ser Val Pro Leu Asn Phe Leu Gly Ser Val Tyr
385                 390                 395                 400
Arg Asp Leu Lys Gln Ser Leu Ile Asp Met Glu Thr Leu Phe Lys Leu
                405                 410                 415
Arg Lys Asn Glu Val Lys Ile Lys Asn Ala Glu Arg Pro Leu Met Leu
                420                 425                 430
Pro Glu Asn Val Pro Tyr Asp Ile Thr Phe Glu Asn Val Thr Phe Gly
                435                 440                 445
Tyr His Pro Asp Arg Lys Ile Leu Lys Asn Ala Ser Phe Thr Ile Pro
        450                 455                 460
Ala Gly Trp Lys Thr Ala Ile Val Gly Ser Ser Gly Ser Gly Lys Ser
465                 470                 475                 480
Thr Ile Leu Lys Leu Val Phe Arg Phe Tyr Asp Pro Glu Ser Gly Arg
                485                 490                 495
Ile Leu Ile Asn Gly Arg Asp Ile Lys Glu Tyr Asp Ile Asp Ala Leu
                500                 505                 510
Arg Lys Val Ile Gly Val Val Pro Gln Asp Thr Pro Leu Phe Asn Asp
                515                 520                 525
Thr Ile Trp Glu Asn Val Lys Phe Gly Arg Ile Asp Ala Thr Asp Glu
        530                 535                 540
Glu Val Ile Thr Val Val Glu Lys Ala Gln Leu Ala Pro Leu Ile Lys
545                 550                 555                 560
Lys Leu Pro Gln Gly Phe Asp Thr Ile Val Gly Glu Arg Gly Leu Met
                565                 570                 575
Ile Ser Gly Gly Glu Lys Gln Arg Leu Ala Ile Ala Arg Val Leu Leu
                580                 585                 590
Lys Asn Ala Arg Ile Met Phe Phe Asp Glu Ala Thr Ser Ala Leu Asp
                595                 600                 605
Thr His Thr Glu Gln Ala Leu Leu Arg Thr Ile Arg Asp Asn Phe Thr
        610                 615                 620
Ser Gly Ser Arg Thr Ser Val Tyr Ile Ala His Arg Leu Arg Thr Ile
625                 630                 635                 640
Ala Asp Ala Asp Lys Ile Ile Val Leu Asp Asn Gly Arg Val Arg Glu
                645                 650                 655
Glu Gly Lys His Leu Glu Leu Leu Ala Met Pro Gly Ser Leu Tyr Arg
                660                 665                 670
Glu Leu Trp Thr Ile Gln Glu Asp Leu Asp His Leu Glu Asn Glu Leu
                675                 680                 685
Lys Asp Gln Gln Glu Leu
                690
```

POLYNUCLEOTIDES ENCODING HUMAN ATP BINDING-CASSETTE TRANSPORT PROTEIN AND METHODS OF USE

FIELD OF THE INVENTION

This invention relates to nucleic acid and amino acid sequences of a human ATP-binding cassette transport protein and to the use of these sequences in the diagnosis, prevention, and treatment of cancer and neuronal disorders.

BACKGROUND OF THE INVENTION

The ATP-binding cassette (ABC) transporters, also called the "traffic ATPases", comprise a superfamily of membrane proteins that mediate transport and channel functions in prokaryotes and eukaryotes (Higgins, C. F. (1992) Annu. Rev. Cell Biol. 8:67–113). ABC proteins share a similar overall structure and significant sequence homology. All ABC proteins contain a conserved domain of approximately two hundred amino acid residues which includes one or more nucleotide binding domains. A majority of these proteins are involved in active transport of molecules across membranes. Eukaryotic ABC proteins include: P-glycoproteins, also known as multidrug resistance (MDR) proteins, which are associated with resistance to a wide range of hydrophobic drugs (MDR1; Gottesman, M. M. & Pastan, I. (1993) Annu. Rev. Biochem. 62:385–427) or with phosphatidylcholine transport (MDR2; Ruetz, S. & Gros, P. (1994) Cell 77:1071–1081); CFTR, the cystic fibrosis transmembrane conductance regulator (Welsh, M. J. & Smith, A. E. (1993) Cell 73:1251–1254); TAP proteins, the transporters associated with antigen processing in mammalian cells (Androlewicz, M. J. et al. (1994) Proc. Natl. Acad. Sci. USA 91:12716–12720); cMOAT/cMRP1, which is associated with transport of glutathione, glucuronide, and sulfate conjugates across the canalicular membrane (Buchler, M. et al. (1996) J. Biol. Chem. 271:15091–15098); and STE6, which exports the a-factor mating pheromone of *S. cerevisiae* (Michaelis, S. (1993) Semin. Cell Biol. 4:17–27). Prokaryotic ABC proteins include periplasmic nutrient permeases, such as those responsible for uptake of maltose (MalFGK) and histidine (HisMPQ) in gram-negative bacteria, and toxin exporters such as those required for export of hemolysin (HlyB) and colicin (ColV) from *E. coli* (Higgins, supra).

Savary, S. et al. (1997; Genomics 41:275–275) recently identified a novel ABC transporter, denoted ABC7, in mouse. The predicted 629 amino acid mouse ABC7 translation product contains six putative transmembrane domains near the N-terminus, followed by an ATP-binding cassette domain. Savary, et al. (supra) also disclosed a partial protein sequence from human similar to the C-terminal 340 amino acids of mouse ABC7 protein. Savary et al. reported that the human ABC7 was widely expressed in cell lines, heart, skeletal muscle, pancreas, lung, liver, and placenta. Human ABC7 expression was not detected in brain.

The discovery of a new human ATP-binding cassette transport protein and the polynucleotides encoding it satisfies a need in the art by providing new compositions which are useful in the diagnosis, prevention and treatment of cancer and neuronal disorders.

SUMMARY OF THE INVENTION

The invention features a substantially purified polypeptide, human ATP-binding cassette transport protein (ABCtxH), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2

In another aspect, the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding ABCtxH under conditions suitable for the expression of the polypeptide; and b) recovering the polypeptide from the host cell culture.

The invention also provides a pharmaceutical composition comprising a substantially purified ABCtxH having the amino acid sequence of SEQ ID NO:1 in conjunction with a suitable pharmaceutical carrier.

The invention also provides a purified antagonist of the polypeptide of SEQ ID NO:1. In one aspect, the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing cancer comprising administering to a subject in need of such treatment an effective amount of an antagonist to ABCtxH.

The invention also provides a method for treating or preventing a neuronal disorder comprising administering to a subject in need of such treatment an effective amount of an antagonist to ABCtxH.

The invention also provides a method for detecting a polynucleotide which encodes ABCtxH in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding ABCtxH in the biological sample. In one aspect, the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of human ATP-binding cassette transport protein, ABCtxH. The alignment was produced using MACDNASIS PRO software (Hitachi Software Engineering Co. Ltd. San Bruno, Calif.).

FIGS. 2A, 2B, 2C, 2D, and 2E show the amino acid sequence alignments among ABCtxH (545981; SEQ ID NO:1), mouse ABC7 (GI 1167982; SEQ ID NO:3), and yeast ATM1 (GI 575393; SEQ ID NO:4), produced using the multisequence alignment program of DNASTAR software (DNASTAR Inc, Madison Wis.).

DESCRIPTION OF THE INVENTION

Figure 3:
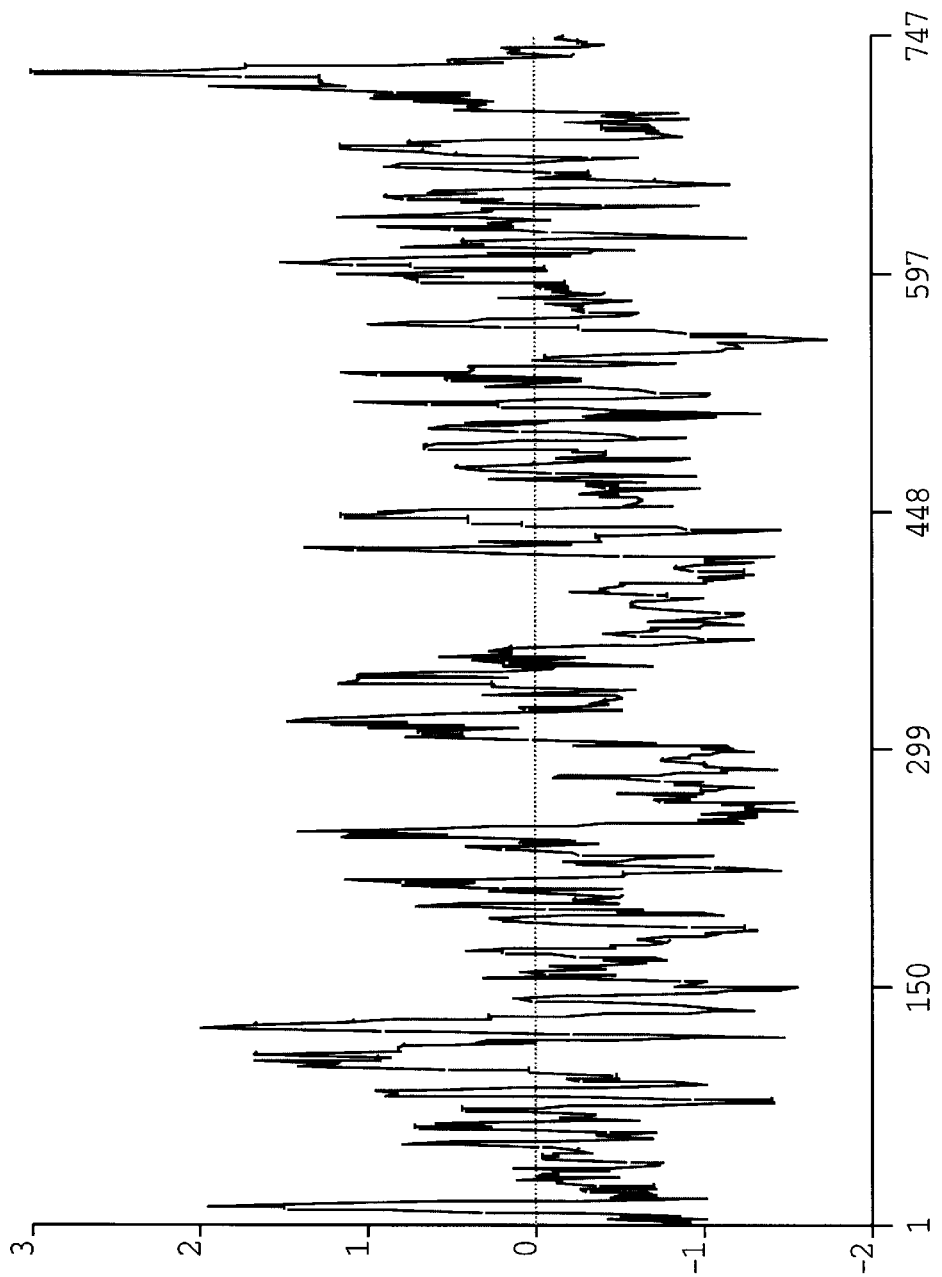
FIG. 3 shows the hydrophobicity plot for ABCtxH, SEQ ID NO:1; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein, and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

ABCtxH, as used herein, refers to the amino acid sequences of substantially purified ABCtxH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to ABCtxH, increases or prolongs the duration of the effect of ABCtxH. Agonists may include proteins, nucleic acids, carbohydrates, or any other molecules which bind to and modulate the effect of ABCtxH.

An "allele" or "allelic sequence", as used herein, is an alternative form of the gene encoding ABCtxH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding ABCtxH as used herein, include those with deletions, insertions, or substitutions of different nucleotides resulting in a polynucleotide that encodes the same or a functionally equivalent ABCtxH. Included within this definition are polymorphisms which may or may not be readily detectable using a particular oligonucleotide probe of the polynucleotide encoding ABCtxH, and improper or unexpected hybridization to alleles, with a locus other than the normal chromosomal locus for the polynucleotide sequence encoding ABCtxH. The encoded protein may also be "altered" and contain deletions, insertions, or substitutions of amino acid residues which produce a silent change and result in a functionally equivalent ABCtxH. Deliberate amino acid substitutions may be made on the basis of similarity in polarity, charge, solubility, hydrophobicity, hydrophilicity, and/or the amphipathic nature of the residues as long as the biological or immunological activity of ABCtxH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein, refers to an oligopeptide, peptide, polypeptide, or protein sequence, and fragment thereof, and to naturally occurring or synthetic molecules. Fragments of ABCtxH are preferably about 5 to about 15 amino acids in length and retain the biological activity or the immunological activity of ABCtxH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to ABCtxH, decreases the amount or the duration of the effect of the biological or immunological activity of ABCtxH. Antagonists may include proteins, nucleic acids, carbohydrates, antibodies or any other molecules which decrease the effect of ABCtxH.

As used herein, the term "antibody" refers to intact molecules as well as fragments thereof, such as Fa, F(ab')$_2$, and Fv, which are capable of binding the epitopic determinant. Antibodies that bind ABCtxH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic ABCtxH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein, refers broadly to any composition containing the given polynucleotide sequence. The composition may comprise a dry formulation or an aqueous solution. Compositions comprising polynucleotide sequences encoding ABCtxH (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding ABCtxH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to ABCtxH or the encoded ABCtxH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of ABCtxH. For example, modulation may cause an increase or a decrease in protein activity, binding characteristics, or any other biological, functional or immunological properties of ABCtxH.

"Nucleic acid sequence" as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length ABCtxH and fragments thereof.

The term "sample", as used herein, is used in its broadest sense. A biological sample suspected of containing nucleic acid encoding ABCtxH, or fragments thereof, or ABCtxH itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of ABCtxH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human ATP-binding cassette transport protein (hereinafter referred to as "ABCtxH"), the polynucleotides encoding ABCtxH, and the use of these compositions for the diagnosis, prevention, or treatment of cancer and neuronal disorders.

Nucleic acids encoding the ABCtxH of the present invention were first identified in Incyte Clone 545981 from the ovarian tissue cDNA library (OVARNOT02) using a computer search for amino acid sequence alignments. A consensus sequence, SEQ ID NO:2, was derived from the following overlapping and/or extended nucleic acid sequences: Incyte Clones 257762 (HNT2RAT01) and 545981 (OVARNOT02).

In one embodiment, the invention encompasses a polypeptide comprising the amino acid sequence of SEQ ID NO:1, as shown in FIGS. 1A, 1B, 1C, 1D, 1E, 1F, and 1G. ABCtxH is 747 amino acids in length and has four potential asn-linked glycosylation sites at residues N 172, N565, N721 and N744; one potential cyclic AMP-dependent protein kinase phosphorylation site at residue S19; seven potential casein kinase-2 phosphorylation sites at residues T410, S569, S605, S632, S636, T664, and S723; and eleven potential protein kinase C phosphorylation sites at residues S3, T46, S55, T112, S216, T337, S362, S504, S538, S704, and S738. As shown in FIGS. 2A, 2B, 2C, 2D, and 2E, ABCtxH has chemical and structural homology with mouse ABC7 (GI 1167982; SEQ ID NO:3) and yeast ATM1 (GI 575393; SEQ ID NO:4). In particular, ABCtxH and mouse ABC7 share 82% identity and ABCtxH and yeast ATM1 share 42% identity. ABCtxH contains 6 potential transmembrane domains within the first 450 amino acids of the N-terminal portion of the protein (FIG. 3). In the C-terminal portion of the protein, ABCtxH contains an ABC transporter sequence signature motif from residues L604 to I618, an ATP/GTP binding site sequence motif A (P-loop) from residues G500 to S507, and an ATP/GTP binding site sequence motif B from residues V612 to A630. Northern analysis shows the expression of ABCtxH in various libraries, which include heart, ovary, and uterus; fetal brain, liver, and spleen; a teratocarcinoma-derived neuronal precursor cell line; a leukemia-derived promonocyte cell line; tumors and tumor-associated tissues from adrenal gland, colon, lung, ovary, pancreas, and thyroid; and Alzheimer's diseased brain.

The invention also encompasses ABCtxH variants. A preferred ABCtxH variant is one having at least 80%, and more preferably at least 90%, amino acid sequence identity to the ABCtxH amino acid sequence (SEQ ID NO:1) and which retains at least one biological, immunological or other functional characteristic or activity of ABCtxl. A most preferred ABCtxH variant is one having at least 95% amino acid sequence identity to SEQ ID NO:1.

The invention also encompasses polynucleotides which encode ABCtxH. Accordingly, any nucleic acid sequence which encodes the amino acid sequence of ABCtxH can be used to produce recombinant molecules which express ABCtxH. In a particular embodiment, the invention encompasses the polynucleotide comprising the nucleic acid sequence of SEQ ID NO:2 as shown in FIGS. 1A, 1B, 1C, 1D, 1E, 1F, and 1G.

It will be appreciated by those skilled in the art that as a result of the degeneracy of the genetic code, a multitude of nucleotide sequences encoding ABCtxH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ABCtxH, and all such variations are to be considered as being specifically disclosed.

Although nucleotide sequences which encode ABCtxH and its variants are preferably capable of hybridizing to the nucleotide sequence of the naturally occurring ABCtxH under appropriately selected conditions of stringency, it may be advantageous to produce nucleotide sequences encoding ABCtxH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ABCtxH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode ABCtxH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding ABCtxH or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding ABCtxH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode ABCtxH may be used in recombinant DNA molecules to direct expression of ABCtxH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express ABCtxH.

As will be understood by those of skill in the art, it may be advantageous to produce ABCtxH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter ABCtxH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding ABCtxH may be ligated to a heterologous sequence to encode a fusion protein. For example, to screen peptide libraries for inhibitors of ABCtxH activity, it may be useful to encode a chimeric ABCtxH protein that can be recognized by a commercially available antibody. A fusion protein may also be engineered to contain a cleavage site located between the ABCtxH encoding sequence and the heterologous protein sequence, so that ABCtxH may be cleaved and purified away from the heterologous moiety.

In another embodiment, sequences encoding ABCtxH may be synthesized, in whole or in part, using chemical methods well known in the art (see Caruthers, M. H. et al. (1980) Nucl. Acids Res. Symp. Ser. 215–223, and Horn, T. et al. (1980) Nucl. Acids Res. Symp. Ser. 225–232). Alternatively, the protein itself may be produced using chemical methods to synthesize the amino acid sequence of ABCtxH, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of ABCtxH, or any part thereof, may be altered during direct synthesis and/or combined using chemical methods with sequences from other proteins, or any part thereof, to produce a variant polypeptide.

In order to express a biologically active ABCtxH, the nucleotide sequences encoding ABCtxH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding ABCtxH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding ABCtxH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector--enhancers, promoters, 5' and 3' untranslated regions--which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ABCtxH, vectors based on SV40 or EBV may be used with an appropriate selectable marker.

In bacterial systems, a number of expression vectors may be selected depending upon the use intended for ABCtxH. For example, when large quantities of ABCtxH are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding ABCtxH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding ABCtxH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express ABCtxH. For example, in one such system, *Autographa californica* nuclear polyhedrosis virus (AcNPV) is used as a vector to express foreign genes in *Spodoptera frugiperda* cells or in *Trichoplusia* larvae. The sequences encoding ABCtxH may be cloned into a non-essential region of the virus, such as the polyhedrin gene, and placed under control of the polyhedrin promoter. Successful insertion of ABCtxH will render the polyhedrin gene inactive and produce recombinant virus lacking coat protein. The recombinant viruses may then be used to infect, for example, *S. frugiperda* cells or *Trichoplusia* larvae in which ABCtxH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding ABCtxH may be ligated into an adenovirus transcription/translation complex consisting of the late promoter and tripartite leader sequence. Insertion in a non-essential E1 or E3 region of the viral genome may be used to obtain a viable virus which is capable of expressing ABCtxH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding ABCtxH. Such signals include the ATG initiation codon and adjacent sequences. In cases where sequences encoding ABCtxH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express ABCtxH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding ABCtxH is inserted within a marker gene sequence, transformed cells containing sequences encoding ABCtxH can be identified by the absence of marker gene function. Alternatively, a marker gene can be placed in tandem with a sequence encoding ABCtxH under the control of a single promoter. Expression of the marker gene in response to induction or selection usually indicates expression of the tandem gene as well.

Alternatively, host cells which contain the nucleic acid sequence encoding ABCtxH and express ABCtxH may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding ABCtxH can be detected by DNA—DNA or DNA-RNA hybridization or amplification using probes or fragments or fragments of polynucleotides encoding ABCtxH. Nucleic acid amplification based assays involve the use of oligonucleotides or oligomers based on the sequences encoding ABCtxH to detect transformants containing DNA or RNA encoding ABCtxH.

A variety of protocols for detecting and measuring the expression of ABCtxH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ABCtxH is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ABCtxH include oligolabeling, nick translation, end-labeling or PCR amplification using a labeled nucleotide. Alternatively, the sequences encoding ABCtxH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding ABCtxH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode ABCtxH may be designed to contain signal sequences which direct secretion of ABCtxH through a prokaryotic or eukaryotic cell membrane. Other constructions may be used to join sequences encoding ABCtxH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ABCtxH may be used to facilitate purification. One such expression vector provides for expression of a fusion protein containing ABCtxH and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying ABCtxH from the fusion protein. A discussion of vectors which contain fusion proteins is provided in Kroll, D. J. et al. (1993; DNA Cell Biol. 12:441–453).

In addition to recombinant production, fragments of ABCtxH may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of ABCtxH may be chemically synthesized separately and combined using chemical methods to produce the full length molecule.

THERAPEUTICS

Chemical and structural homology exists among ABCtxH, mouse ABC7 (GI 1167982) and yeast ATM1 (GI 575393). In addition, ABCtxH is expressed in fetal tissues, cell lines, cancers, and diseased brain. Therefore, ABCtxH appears to function as a ABC-type transport protein and may play a role in disease-related transport processes, particularly in cancers and neuronal disorders.

In one embodiment, an antagonist of ABCtxH may be administered to a subject to prevent or treat cancer. Such cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds ABCtxH may be used directly as an antagonist or indirectly as a targeting or delivery mechanism for bringing a pharmaceutical agent to cells or tissue which express ABCtxH.

In another embodiment, a vector expressing the complement of the polynucleotide encoding ABCtxH may be administered to a subject to treat or prevent cancer including, but not limited to, those described above.

In another embodiment, an antagonist of ABCtxH may be administered to a subject to prevent or treat a neuronal disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. In one aspect, an antibody which specifically binds ABCtxH may be used directly as an antagonist or indirectly as a targeting or delivery mechanism for bringing a pharmaceutical agent to cells or tissue which express ABCtxH.

In another embodiment, a vector expressing the complement of the polynucleotide encoding ABCtxH may be administered to a subject to treat or prevent a neuronal disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of ABCtxH may be produced using methods which are generally known in the art. In particular, purified ABCtxH may be used to produce antibodies or to screen libraries of pharmaceutical agents to identify those which specifically bind ABCtxH.

Antibodies to ABCtxH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ABCtxH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to ABCtxH have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of ABCtxH amino acids may be fused with those of another protein such as keyhole limpet hemocyanin and antibody produced against the chimeric molecule.

Monoclonal antibodies to ABCtxH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce ABCtxH-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for ABCtxH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ABCtxH and its specific antibody. A two-site, monoclonal-based immunoassay utilizing monoclonal antibodies reactive to two non-interfering ABCtxH epitopcs is preferred, but a competitive binding assay may also be employed (Maddox, supra).

In another embodiment of the invention, the polynucleotides encoding ABCtxH, or any fragment or complement thereof, may be used for therapeutic purposes. In one aspect, the complement of the polynucleotide encoding ABCtxH may be used in situations in which it would be desirable to block the transcription of the mRNA. In particular, cells may be transformed with sequences complementary to polynucleotides encoding ABCtxH. Thus, complementary molecules or fragments may be used to modulate ABCtxH activity, or to achieve regulation of gene function. Such technology is now well known in the art, and sense or antisense oligonucleotides or larger fragments, can be designed from various locations along the coding or control regions of sequences encoding ABCtxH.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding ABCtxH. These techniques are described both in Sambrook et al. (supra) and in Ausubel et al. (supra).

Genes encoding ABCtxH can be turned off by transforming a cell or tissue with expression vectors which express high levels of a polynucleotide or fragment thereof which encodes ABCtxH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding ABCtxH (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ABCtxH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding ABCtxH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ABCtxH, antibodies to ABCtxH, mimetics, agonists, antagonists, or inhibitors of ABCtxH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ABCtxH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example ABCtxH or fragments thereof, antibodies of ABCtxH, agonists, antagonists or inhibitors of ABCtxH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind ABCtxH may be used for the diagnosis of conditions or diseases characterized by expression of ABCtxH, or in assays to monitor patients being treated with ABCtxH, agonists, antagonists or inhibitors. The antibodies useful for diagnostic purposes may be prepared in the same manner as those described above for therapeutics. Diagnostic assays for ABCtxH include methods which utilize the antibody and a label to detect ABCtxH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ABCtxH are known in the art and provide a basis for diagnosing altered or abnormal levels of ABCtxH expression. Normal or standard values for ABCtxH expression are established by combining body fluids or cell extracts taken from normal mammalian subjects, preferably human, with antibody to ABCtxH under conditions suitable for complex formation. The amount of standard complex formation may be quantified by various methods, but preferably by photometric means. Quantities of ABCtxH expressed in subject samples, control and disease from biopsied tissues are compared with the standard values. Deviation between standard and subject values establishes the parameters for diagnosing disease.

In another embodiment of the invention, the polynucleotides encoding ABCtxH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of ABCtxH may be correlated with disease. The diagnostic assay may be used to distinguish between absence, presence, and excess expression of ABCtxH, and to monitor regulation of ABCtxH levels during therapeutic intervention.

In one aspect, hybridization with PCR probes which are capable of detecting polynucleotide sequences, including genomic sequences, encoding ABCtxH or closely related molecules, may be used to identify nucleic acid sequences which encode ABCtxH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ABCtxH, alleles, or related sequences.

Probes may also be used for the detection of related sequences, and should preferably contain at least 50% of the nucleotides from any of the ABCtxH encoding sequences. The hybridization probes of the subject invention may be DNA or RNA and derived from the nucleotide sequence of SEQ ID NO:2 or from genomic sequence including promoter, enhancer elements, and introns of the naturally occurring ABCtxH.

Means for producing specific hybridization probes for DNAs encoding ABCtxH include the cloning of nucleic acid sequences encoding ABCtxH or ABCtxH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding ABCtxH may be used for the diagnosis of conditions or disorders which are associated with expression of ABCtxH. Examples of such conditions or disorders include adenocarcinoma, leukemia, lymphoma, melanoma, myeloma, sarcoma, teratocarcinoma, and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. The polynucleotide sequences encoding ABCtxH may be used in Southern or northern analysis, dot blot, or other membrane-based technologies; in PCR technologies; or in dipstick, pin, ELISA assays or microarrays utilizing fluids or tissues from patient biopsies to detect altered ABCtxH expression. Such qualitative or quantitative methods are well known in the art.

In a particular aspect, the nucleotide sequences encoding ABCtxH may be useful in assays that detect activation or induction of various cancers, particularly those mentioned above. The nucleotide sequences encoding ABCtxH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding ABCtxH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ABCtxH, a normal or standard profile for expression is established. This may be accomplished by combining body fluids or cell extracts taken from normal subjects, either animal or human, with a sequence, or a fragment thereof, which encodes ABCtxH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding ABCtxH may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of ABCtxH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Ileller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251,116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode ABCtxH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding ABCtxH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, ABCtxH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ABCtxH and the agent being tested, may be measured.

Another technique for drug screening which may be used provides for high throughput screening of compounds having suitable binding affinity to the protein of interest as described in published PCT application WO84/03564. In this method, as applied to ABCtxH large numbers of different small test compounds are synthesized on a solid substrate, such as plastic pins or some other surface. The test compounds are reacted with ABCtxH, or fragments thereof, and washed. Bound ABCtxH is then detected by methods well known in the art. Purified ABCtxH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding ABCtxH specifically compete with a test compound for binding ABCtxH. In this manner, the antibodies can be used to detect the presence of any peptide which shares one or more antigenic determinants with ABCtxH.

In additional embodiments, the nucleotide sequences which encode ABCtxH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I OVARNOT02 cDNA Library Construction

The cDNA library was constructed from ovarian tissue removed from a 59 year old Caucasian female (lot #94-042) obtained from Keystone Skin Bank (International Institute for the Advancement of Medicine, Exton Pa.). The tissue was flash frozen, ground in a mortar and pestle, and lysed immediately in a buffer containing guanidinium isothiocyanate. The lysate was extracted twice with a mixture of phenol and chloroform, pH 8.0, and centrifuged over a CsCl cushion using a Beckman SW28 rotor in a L8-70M Ultracentrifuge (Beckman Instruments). The RNA was precipitated from 0.3M sodium acetate using 2.5 volumes of ethanol, resuspended in water and treated with DNase for 15 min at 37° C. The poly A+RNA was isolated with the Qiagen OLIGOTEX kit (QIAGEN Inc, Chatsworth Calif.) and used to construct the cDNA library.

The RNA was handled according to the recommended protocols in the SuperScript Plasmid System (catalog #18248-013; Gibco/BRL). Selected cDNAs exceeding 400 bp were ligated into the vector, PSPORT I, and the plasmid was subsequently transformed into DH5a competent cells (Cat. #18258-012, GIBCO/BRL).

II Isolation and Sequencing of cDNA Clones

Plasmid DNA was purified using the Miniprep Kit (Catalogue #77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog #22711, GIBCO/BRL) with carbenicillin at 25 mg/L and glycerol at 0.4%. After the wells were inoculated, the bacteria were cultured for 24 hours and lysed with 60 $\mu$l of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against Gen-Bank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding ABCtxH occurs. Abundance and percent abundance are also reported. Abundance directly reflects the number of times a particular transcript is represented in a cDNA library, and percent abundance is abundance divided by the total number of sequences examined in the cDNA library.

V Extension of ABCtxH Encoding Polynucleotides

The nucleic acid sequence of the Incyte Clone 545981 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 μl of liquid LB/2x Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMATAR film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the ABCtxH-encoding sequence, or any part thereof, is used to decrease or inhibit expression of naturally occurring ABCtxH. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of ABCtxH, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the ABCtxH-encoding transcript.

IX Expression of ABCtxH

Expression of ABCtxH is accomplished by subcloning the cDNAs into appropriate vectors and transforming the vectors into host cells. In this case, the cloning vector is also used to express ABCtxH in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein.

X Demonstration of ABCtxH Activity

ATP binding to ABCtxH may be measured by photoaffinity labeling with 8-azido-ATP ($N_3$ATP) in a competition assay. Reaction mixtures containing 1 mg/ml ABCtxH are incubated with varying concentrations of ATP or the nonhydrolyzable ATP analog adenyl-5'-imidodiphosphate for 10 minutes at 4° C. A mixture of $N_3$ATP (Sigma Chemical Corp., St. Louis Mo.) plus $N_3[\alpha$-$^{32}$P]ATP (5 mCi/μmol; ICN, Irvine Calif.) is added to a final concentration of 100 μM and 0.5 ml aliquots are placed in the wells of a porcelain spot plate on ice. The plate is irradiated using a short wave 254 nm UV lamp (Ultraviolet Products, San Gabriel Calif.) at a distance of 2.5-cm from the plate for two one-minute intervals with a one-minute cooling interval in between. The reaction is stopped by addition of dithiothreitol to a final concentration of 2 mM. The incubations are subjected to SDS-PAGE electrophoresis (Sambrook, supra). The gel is dried and autoradiographed. Protein bands corresponding to ABCtxH are excised and radioactivity is quantitated. The decrease in radioactivity with increasing ATP or adenyl-5'-imidodiphosphate provides a measure of ATP affinity to ABCtxH.

XI Production of ABCtxH Specific Antibodies

ABCtxH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring ABCtxH Using Specific Antibodies

Naturally occurring or recombinant ABCtxH is substantially purified by immunoaffinity chromatography using antibodies specific for ABCtxH. An immunoaffinity column is constructed by covalently coupling ABCtxH antibody to an activated chromatographic resin, such as CNBr-activated SEPHAROSE (Pharmacia & Upjohn). After the coupling, the resin is blocked and washed according to the manufacturer's instructions.

Media containing ABCtxH is passed over the immunoaffinity column, and the column is washed under conditions that allow the preferential absorbance of ABCtxH (e.g., high ionic strength buffers in the presence of detergent). The column is eluted under conditions that disrupt antibody/ABCtxfl binding (eg, a buffer of pH 2–3 or a high concentration of a chaotrope, such as urea or thiocyanate ion), and ABCtxH is collected.

XIII Identification of Molecules Which Interact with ABCtxH

ABCtxH or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled ABCtxH, washed and any wells with labeled ABCtxH complex are assayed. Data obtained using different concentrations of ABCtxH are used to calculate values for the number, affinity, and association of ABCtxH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the human ATP-binding cassette transport protein comprising the amino acid sequence of SEO ID NO:1.

2. A composition comprising the polynucleotide sequence of claim 1.

3. An isolated and purified polynucleotide sequence which is complementary to the polynucleotide sequence of claim 1.

4. An isolated and purified polynucleotide sequence comprising SEQ ID NO:2.

5. An isolated and purified polynucleotide sequence which is complementary to the polynucleotide sequence of claim 4.

6. An expression vector containing the polynucleotide sequence of claim 1.

7. A host cell containing the vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

9. A method for detecting a polynucleotide which encodes human ATP-binding cassette transport protein in a biological sample comprising the steps of:

a) hybridizing the polynucleotide of claim 3 to nucleic acid material of a biological sample, thereby forming a hybridization complex; and b) detecting said hybridization complex, wherein the presence of said complex correlates with the presence of a polynucleotide encoding human ATP-binding cassette transport protein in said biological sample.

10. The method of claim 9 wherein the nucleic acid material is amplified by the polymerase chain reaction prior to hybridization.

* * * * *